US012599294B2

(12) United States Patent
Schwärzle et al.

(10) Patent No.: US 12,599,294 B2
(45) Date of Patent: Apr. 14, 2026

(54) IMAGE-RECORDING DEVICE FOR IMPROVED LOW LIGHT INTENSITY IMAGING AND ASSOCIATED IMAGE-RECORDING METHOD

(71) Applicant: SCHÖLLY FIBEROPTIC GMBH, Denzlingen (DE)

(72) Inventors: Michael Schwärzle, Denzlingen (DE); Matthias Kühn, Freiburg (DE); Johannes Bourbon, Freiburg (DE); Stefan Schröer, Freiburg (DE); Lutz Labusch, Emmendingen (DE)

(73) Assignee: SCHÖLLY FIBEROPTIC GMBH, Denzlingen (DE)

( * ) Notice: Subject to any disclaimer, the term of this patent is extended or adjusted under 35 U.S.C. 154(b) by 207 days.

(21) Appl. No.: 17/862,674

(22) Filed: Jul. 12, 2022

(65) Prior Publication Data

US 2023/0013267 A1 Jan. 19, 2023

(30) Foreign Application Priority Data

Jul. 16, 2021 (DE) ..................... 10 2021 118 427.4

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00009* (2013.01); *H04N 13/128* (2018.05);
(Continued)

(58) Field of Classification Search
CPC . A61B 1/05; A61B 1/00009; A61B 2562/046; A61B 1/00186; A61B 1/043;
(Continued)

(56) References Cited

U.S. PATENT DOCUMENTS

2001/0035871 A1* 11/2001 Bieger .................. A61B 1/0005
348/E5.056
2017/0176334 A1* 6/2017 Mattioli Della Rocca ...................
G01J 3/4406
(Continued)

FOREIGN PATENT DOCUMENTS

WO 2015052523 4/2015
WO 2017174998 10/2017

OTHER PUBLICATIONS

German Office Action dated Oct. 22, 2024 from corresponding Application No. 10 2021 118 427.4.

*Primary Examiner* — Shahan Ur Rahaman
(74) *Attorney, Agent, or Firm* — Grogan, Tuccillo & Vanderleeden, LLP

(57) ABSTRACT

In order to improve imaging, in particular for low light intensities, an image recording device, in particular formed as an endoscope, is proposed, which comprises a single photon sensitive detector (SPSD) in addition to an image sensor, which uses photodiodes as light-sensitive cells, in order to respectively detect light from a common object area. With the help of the SPSD, additional image information can be obtained from the object area, to improve the image data recorded with the image sensor or to enhance it with additional image information, in particular with regard to a further spectral range, which is captured with the SPSD.

24 Claims, 3 Drawing Sheets

Figure 1:
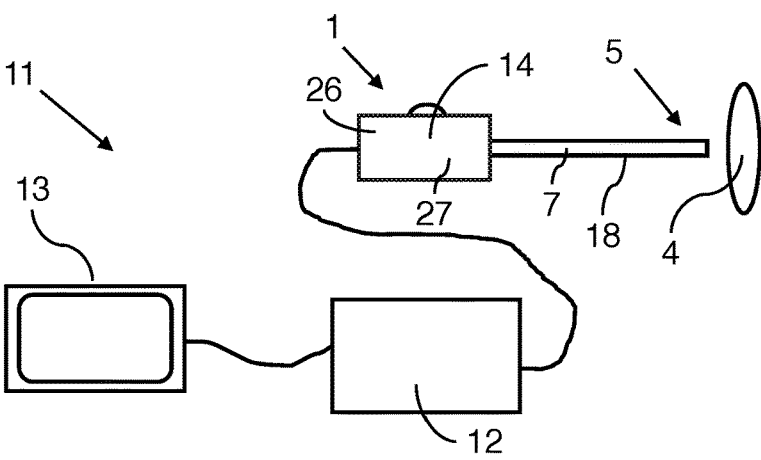

(51) Int. Cl.

| | | |
|---|---|---|
| *H04N 13/128* | (2018.01) | |
| *H04N 13/156* | (2018.01) | |
| *H10F 39/00* | (2025.01) | |
| *H10F 39/18* | (2025.01) | |

(52) U.S. Cl.

CPC ......... *H04N 13/156* (2018.05); *H10F 39/182* (2025.01); *H10F 39/8053* (2025.01); *A61B 2562/046* (2013.01)

(58) Field of Classification Search

CPC ............ A61B 1/0638; H01L 27/14621; H01L 27/14645; H04N 13/128; H04N 13/156; H04N 13/239; H04N 23/16; H04N 23/11

See application file for complete search history.

(56) References Cited

U.S. PATENT DOCUMENTS

| | | | | |
|---|---|---|---|---|
| 2019/0159663 A1* | 5/2019 | Krstajic | ............... | A61B 5/0071 |
| 2019/0204572 A1* | 7/2019 | Hermalyn | ............ | G02B 17/008 |
| 2021/0168276 A1* | 6/2021 | Duckett, III | ........... | H04N 23/45 |
| 2021/0389244 A1* | 12/2021 | Bowman | ............... | G01S 17/894 |
| 2022/0361952 A1* | 11/2022 | Shademan | .............. | G06T 19/20 |

* cited by examiner

IMAGE-RECORDING DEVICE FOR IMPROVED LOW LIGHT INTENSITY IMAGING AND ASSOCIATED IMAGE-RECORDING METHOD

CROSS REFERENCE TO RELATED APPLICATIONS

This application claims priority to German Patent Application No. 10 2021 118 427.4, filed on Jul. 16, 2021, all of which is hereby incorporated by reference in its entirety.

BACKGROUND

The invention firstly relates to an image-recording device, in particular arranged for imaging in medical applications, with at least one image sensor whose pixels are based on photodiodes. For example, this image-recording device can be formed as an endoscope or as an exoscopic imaging system (i.e., an exoscope). Additionally or alternatively, the image-recording device can also be formed as a multi-spectral imaging system.

The invention further relates to an associated image-recording method, which can be carried out in particular with such an image-recording device/such an endoscope/exoscope. In this method, a first image, preferably a color image, is captured by means of an image sensor (in particular the aforementioned), whose pixels are based on photo-diodes.

In the prior art, image-recording devices are already known as described above, for example in the form of an endoscope. Due to the small diameter, the high number of lenses in the optical system of the endoscope and the small pixel size of the miniaturized image sensors used, the available light quantity is a limiting factor. So far, this has often been compensated for by using very bright light sources, or—on the side of the image sensor—by increasing the electronic gain. The high amount of light, which in the first case must be brought from the light source to the endoscope tip or generated by appropriately powerful LEDs in the endoscope tip, causes a strong self-heating of the endoscope. This self-heating is often problematic, especially in medical applications; as is the case for an increase in the electronic gain, self-heating also has a negative effect on the signal-to-noise ratio of the image sensor. Therefore, today's endoscopes often operate at the limit of system performance, especially in applications with very low signal responses, for example when recording fluorescent light.

Previously known image-recording devices that can detect very small amounts of light still suffer from insufficient image resolution for many applications, which is particularly problematic in the area of endoscopy. The size of previously used sensors is also often unsuitable for endoscopy.

SUMMARY

Based on the above, the invention is therefore based on the task of providing an image-recording device, in particular for medical endoscopy, that provides an increased image brightness and an increased image contrast, in particular in applications such as fluorescent light imaging, in which very small amounts of light must be detected.

In order to solve this problem for an image-recording device, the features of claim 1 are provided according to the invention. In particular, according to the invention, the task is solved for an image recording device of the type mentioned above, in particular for an endoscope or exoscope, by proposing that the image-recording device has a single photon sensitive detector (SPSD) and that the image sensor and the SPSD are (each) equipped to detect light from a common object area (which can in particular lie outside the image-recording device).

A field of view that can be detected with the SPSD can in this case be different (in particular smaller) from a second field of view that can be detected with the image sensor. In the common object area, the two fields of view overlap, i.e., both the SPSD and the image sensor detect the common object area.

The image sensor can for example be embodied as a conventional RGB CMOS sensor or as a monochromatic black-white image sensor. Furthermore, the image sensor (in particular for otherwise monochromatic configurations) can also—depending on the specific application—be equipped with additional spectral filters, in particular with filter arrays, in order to obtain spectrally resolved image information.

This approach can also be applied, for example, to exoscopes that—unlike endoscopes—are not introduced into body cavities but are typically placed at a distance of, for example, 25 to 75 cm from the surgical site by means of a holding arm in order to give the surgeon large freedom of movement in the workspace.

In other words, it is proposed to capture image information from a common object area (which can thus also be at a distance to the optical imaging unit) or from a common field of view in parallel and simultaneously with an ordinary image sensor and additionally with an SPSD in order to calculate high-resolution, and simultaneously high-contrast and bright images from this data. These images can therefore be understood as synthetic images because they are synthesized from output signals from the image sensor and the SPSD. The image information captured with the highly-sensitive SPSD is in this case specifically used to enhance the high-resolution image of the image sensor with regard to image brightness and contrast.

While the SPSD then offers high sensitivity, at presently still comparatively low resolution, the image information recorded with the image sensor can serve to improve the resolution of the image to be calculated and/or to provide required color information, for example to generate a white light image. It goes without saying that said image-recording device can correspondingly have an image processing unit that is correspondingly arranged to increase a resolution of an image to be calculated based on image information of the SPSD and the image sensor and/or to calculate additional color information.

The invention has thus recognized that, for example, information on a particular fluorescent light source is not always required at a very high resolution. For example, it may be sufficient for a surgeon to only approximately locate a very weak fluorescent light source that is also hidden among other tissue layers by using the image recording device, because he can then decide on the basis of the higher-resolution, visible image how to approach the light source of the fluorescent source in order to examine it in greater detail (e.g., to examine malignant tissue marked with a fluorescent dye).

It is then advantageous that even applications that must detect very small amounts of light—such as the classic fluorescent light imaging, fluorescence lifetime imaging microscopy (FLIM) or time-of-flight (ToF) measurements, in particular for generating 3D images—can obtain high-resolution images of good image quality with respect to signal-to-noise-ratio (SNR) and image contrast, while also having the ability to detect very low light intensities. This is the case because single photon sensitive detectors (SPS), such as photomultipliers, typically have a detection threshold for light lower by several orders of magnitude compared to classic CMOS image sensors such that SPSDs are able to detect individual photons. In recent years, the development of SPSD has advanced significantly, and miniaturized SPSDs are available based on CMOS technology, which offer a comparatively high local resolution.

However, SPSDs can also be designed as single detectors in the form of an array and can be fully integrated as an image sensor chip, for example on the basis of individual detectors such as SPADs (silicon photon avalanche diodes) or SiPMs (silicon photomultipliers). Such technologies are therefore suitable for 2D imaging of individual photons. Furthermore, an SPSD can also have "on chip" analysis electronics, typically based on CMOS technology.

According to the invention, a combination of at least one classic CMOS image sensor with an SPSD array, for example in the form of an SPAD array, can drastically increase the light yield, while at the same time guaranteeing high resolution by taking advantage of the comparatively small pixels of the classic image sensor. A high-resolution, bright and high-contrast image can then be generated from the measurement data of the at least one classic CMOS image sensor and the SPSD array. One possible application example for this is an "overlay" (image overlay) of fluorescent image data (low signal level) recorded with the SPSD and high resolution white light image data recorded using the CMOS image sensor.

According to the invention, the task can also be solved by further advantageous embodiments according to the dependent claims.

For example, it is advantageous for a simplified calculation of the image when the image sensor and the SPSD are positioned or arranged in a fixed spatial relationship to each other. The image sensor and the SPSD can then be arranged in a distal end area of the image-recording device spatially fixed in relation to each other, for example when the image recording device is designed as a chip-in-tip endoscope. But depending on the size, in particular of the SPSD and/or the image sensor, embodiments can also be advantageous when the image sensor and the SPSD are arranged spatially fixed in relation to each other in a proximal end area of the image recording device.

Another option that can be used additionally or alternatively is to arrange the image sensor and the SPSD spatially fixed in relation to a beam splitter. This enables the beam splitter to forward light from the common object area to the image sensor and to the SPSD. This approach enables using a common optical imaging unit for the image sensor and the SPSD.

A particularly preferred embodiment, which results in a compact design, provides that the image sensor and the SPSD are arranged on exterior surfaces of the beam splitter and/or corresponding to a common intermediate image plane of an optical imaging unit.

The image sensor and the SPSD can either be arranged directly on the beam splitter (i.e., in contact with the latter) or also with a slight air gap to the beam splitter on the outer surfaces of the beam splitter, depending on the optical design of the imaging beam path. The respective imaging beam path is preferably designed such that the image sensor and the SPSD can image/detect a common object area. The SPSD can in this case image only a partial area of the field of view of the image sensor, or vice versa. Depending on the design, it may also be necessary for the image sensor and/or the SPSD to each have a slight offset in the direction of the respective optical axis of the imaging beam path, since different wavelength ranges to be detected (e.g., VIS vs. NIR range) can cause a shift of the image plane, which can then be compensated accordingly by the offset.

Accordingly, the image-recording device can have a common optical imaging unit—in particular arranged in a distal end area of the image-recording device or the endoscope/exoscope—that conducts light from the common object area to the image sensor and to the SPSD.

Alternatively, two (or more) separate light conducting channels image-recording device/the endoscope/the exoscope, which respectively conduct light from the common object area to the image sensor or to the SPSD.

According to another specific embodiment, a stereo image-recording device can also be obtained for generating 3D image data that follows the concept according to the invention. This stereo image-recording device has an image-recording device designed according to the invention, each having an SPSD and an image sensor that detects light from a common object area. But it is for example also possible to use only one (larger) image sensor whose image sensor surface is divided into two sub-regions, which are then used by the respective image-recording device as the image sensor. The two image-recording devices of the stereo image-recording device formed according to the invention are arranged for stereoscopic imaging. In other words, the two image-recording devices can thus differ in a respective image recording angle (or viewing angle). As a result, depth information and thus 3D image data can be obtained from a matching object area that is detected/observed by both image-recording devices.

The image sensor can preferably be formed as an active pixel sensor (APS) with integrated amplifier circuit.

It can further be provided that the image sensor outputs a black-white image or a color image, in particular by using a color filter array (CFA). Such a CFA can be e.g., formed as a classic RGB-Bayer-pattern, or by means of CMY color filters.

Furthermore, the image sensor can also be formed to detect wavelengths in adjacent wavelength ranges, in particular in the ultraviolet or infrared wavelength range, either in addition to wavelengths in the visible range or alternatively to wavelengths in the visible range.

In order to enable a sufficient spatial resolution of very weak light signals, such as fluorescent light pulses, it is advantageous if the SPSD is formed as a 2D arrangement of individual detectors, preferably fully integrated and/or based on semiconductor technology (for example based on silicon (Si) or gallium arsenide (GaAs), and which can each detect individual photons. As mentioned above, these detectors can in particular be formed as SPADs (silicon photon avalanche diodes) or SiPMs (silicon photomultipliers) and can be arranged as a 2D detector array. In such embodiments, the SPSD can thus provide 2D image data, which can in particular be used to enhance the presentation of 2D image data of the image sensor (image enhancement).

Accordingly, the SPSD can be realized on the basis of single photon avalanche diodes (SPAD) and/or silicon photomultipliers (SiPM), in particular as a 2D SPAD array or a 2D SiPM array.

The image sensor and/or the SPSD can also be realized using CMOS technology, preferably in each case as a fully integrated electronic module and/or with integrated signal processing electronics.

In the current prior art, a sensible selection of components for the image-recording device could be that the image sensor has pixels with a size of less than 5 µm, preferably less than 2 µm, and/or wherein the SPSD can have pixels with a size of more than 5 µm, preferably more than 10 µm. This represents a currently common compromise with regard to high resolution of the image sensor and high light sensitivity of the SPSD, with simultaneously compact design. However, it cannot be ruled out that in the near future, technological developments will in particular continue to reduce the pixel size of SPSDs, while maintaining good sensitivity, which would lead to a higher resolution of this signal component/this image information.

Currently, for example, the resolution of the image sensor can still be at least a factor of 5, preferably at least a factor of 10, higher than a resolution of the SPSD; further increases in the near future do not appear to be beyond reason, which underlines the technical advantage of the concept presented here.

In certain applications, such as when the image-recording device has a light source for emitting excitation light, it may be useful for the image-recording device to have at least one optical filter, such as a band-pass filter or a band-block filter.

Such a filter can be used to keep undesired light, such as the excitation light required in fluorescent light imaging from the object area from the SPSD and/or from the image sensor. For example, a fluorescent marker with a particular wavelength or range of wavelengths can be excited and then emit fluorescent light with a different, higher wavelength. If this fluorescent response is now to be detected, the excitation wavelength can be blocked by forming said filter as a band block. The filter can then filter the excitation light out of the respective imaging beam path (of the SPSD and/or the image sensor) and thus prevent the excitation light from falsifying the fluorescent light response.

For example, one or more such filters can also ensure that the image sensor detects light only in a first spectral range (especially in the visible spectrum), while the SPSD detects light in a second spectral range (e.g., in the UV or NIR wavelength range) that deviates from the first spectral range. The filter can thus in particular serve to keep unwanted light away from the SPSD such that it is not flooded or saturated by such interference light. As a result, the SPSD can selectively detect even the smallest amount of light of the desired wavelengths with high sensitivity and thus operate far below the typical sensitivity limit of conventional image sensors.

Said at least one optical filter can thus be arranged/formed to select a (limited) wavelength range that is captured by the SPSD and/or the image sensor. In this case, the optical filter can for example be embodied as a band-pass filter.

Such a filter can then in particular be provided for the optical path of the SPSD and the optical path of the image sensor. These filters can of course have different characteristics, in particular different spectral transmission windows.

Of course, these approaches can also be combined so that, for example, a narrow band-pass filter can firstly be used to select the wavelength range that is captured by the SPSD and secondly to keep undesired light, such as excitation light, away from the SPSD. In particular, multi-band pass or multi-band blocks can also be used as filters to either pass or block multiple wavelengths.

According to a preferred embodiment, the image sensor is arranged for imaging in the visible wavelength range (VIS). This allows a surgeon using the image-recording device to quickly and easily navigate within a surgical site using VIS imaging. In such a case, the SPSD may be equipped for imaging in a non-visible wavelength range, particularly in the UV or NIR range. In particular, this enables the detection of additional spectral information with the SPSD, for example in the form of a fluorescence image overlayed on a white light image captured by the image sensor.

In principle, it is possible to detect light from the NIR wavelength range using either the image sensor or the SPSD. However, the SPSD offers a significantly lower detection threshold, so that—especially at low light intensities in this wavelength range, which is of interest for many applications—only the SPSD is able to detect very weak NIR signals, such as NIR fluorescent light emitted by a specific tissue type. Initially, only the lower resolution of the SPSD compared to the image sensor is disadvantageous.

Nevertheless, in practice, it may make sense to also form the image sensor such that it can still detect NIR wavelengths. This can for example be achieved by raising the usual cut-off wavelength of a cut-off filter of the image sensor to more than 850 nm or—depending on the application—by completely eliminating a cut-off filter. In such an embodiment of the image-recording device, this can advantageously be used to visualize objects located at greater depth by means of fluorescence imaging provided by the SPSD, which cannot yet be "seen"/detected by the image sensor due to their concealment by superficial tissue layers (and the associated signal attenuation). If the superficial tissue is then removed, the user can benefit from the higher resolution of the image sensor, because the user can then also detect the NIR signal due to the now higher signal intensity of the fluorescent light. In other words, a surgeon can thus initially roughly trace a fluorescent light source in the tissue using the SPSD and, after a tissue resection has taken place, examine the fluorescent tissue in more detail using the image sensor.

For example, the at least one optical filter can be realized particularly simply on a beam splitter, in particular the one mentioned above, as an optical thin film.

A more advanced embodiment provides that the at least one optical filter is actively tunable. In this case, the spectral range that passes the filter and is then recorded by the SPSD can therefore be actively selected. Depending on the tuning of the optical filter, different wavelengths (especially at different times) can then for example be detected by the SPSD. This is useful, for example, in applications where the SPSD is to specifically detect a first fluorescence wavelength, or a second fluorescence wavelength different from the first fluorescence wavelength, since the sensitivity of the SPSD can thus be set spectrally by tuning the filter.

According to a particularly simple embodiment, a rotating filter wheel can also be provided with which certain wavelengths can be selected. Such an embodiment of the tunable optical filter can be suitable, for example, if the image-recording device is formed as an exoscope (e.g., surgical microscope).

Another embodiment proposes that the image-recording device has (at least) two SPSDs arranged separately from each other. In this case, it is preferred that the two SPSDs specifically detect different wavelength ranges, in particular due to two different optical filters (through which light reaches the respective SPSD). These two SPSDs can each be formed as described above.

The image-recording device can also have (at least) two image sensors (spatially) arranged separately from each other. In this case, it is preferred that the two image sensors also detect different wavelength ranges/spectral ranges. For this purpose, the two image sensors can also have different color filters at the pixel level (i.e., different color filter arrays—CFAs).

Lastly, as already mentioned, it is advantageous if the image recording device, in particular the endoscopic or exoscopic, optionally multispectral, image-recording device, has an image computation unit that is designed to calculate and output a synthetic image from signals of the image sensor and from signals of the SPSD. This simplifies the use of the image-recording device.

Image recording methods according to the invention are now presented below. Therefore, it should be noted in advance that the image-recording device can in particular have the necessary means and can be equipped to perform any of the methods described below or a method according to any of the claims referencing a method, in particular by automated means.

In order to solve the above-mentioned task, an image-recording method of the type mentioned above is also proposed, wherein a first image is recorded using an image sensor of an image-recording device. This method is characterized in that a second image is captured using a single photon sensitive detector (SPSD) of the image-recording device, and a synthetic image is calculated and output from the first image and the second image, preferably from said image computation unit.

One possible example of such a method is to generate an "overlay" (image overlay) of fluorescence image data (with typically low signal level) recorded with the SPSD and of high resolution white light image data recorded using the image sensor. A fluorescence image that would normally not be visible in the white light image due to the low signal intensity is then captured with the SPSD and overlaid on the white light image recorded with the image sensor. This overlay may also include, for example, a false color representation of the fluorescence image and/or the portions of the fluorescence image and the white light image may be assigned a different weight factor.

The method described above thus results in simultaneously bright, high-contrast, and high-resolution images, which can in particular represent image information from different (non-overlapping) wavelength ranges, such as in the VIS and NIR range, in order to provide the user with enhanced imaging.

Since the resolutions of the two images are usually different, it can be provided that the second image is scaled (in particular upscaled, namely when the resolution of the first image exceeds that of the second image) to an image resolution of the first image before synthesis. In the prior art, white image sensors usually have a significantly higher resolution than the SPSD, i.e., the resolution must be adjusted, for example to generate an overlay of the images. In addition, as already described above, the image section captured by the SPSD can be a subset of the field of view that can be recorded with the image sensor. In this case, the overlay of the image data of the SPSD can also only concern this image section; in this special case, a scaling must therefore at most be carried out with respect to this image section, but not with respect to the overall image of the image sensor.

The synthetic image can further be obtained, for example, by an overlay, in particular by uniting the first image with the second image.

Another optional method variant when calculating the synthetic image, preferably by means of an alpha-blending method, is to also take into account alpha values as a metric for the transparency or opacity of respective pixels in addition to color information.

The method is particularly advantageous when the SPSD detects fluorescent light, in particular autofluorescent light.

In this case, an excitation light used for fluorescence imaging can be separated and filtered from the fluorescent light by means of an optical filter, even before the fluorescent light reaches the SPSD. This allows the SPSD to selectively detect the fluorescent light from the excitation light. This is particularly useful if the excitation light is also partially used to illuminate the observed scene and is detected with the image sensor.

It can also be provided in individual applications that at least one third image, which was captured with an additional image sensor or an additional SPSD of the image-recording device, in particular in an additional wavelength range, is taken into account for the synthesis of the synthetic image. In such an embodiment of the method wherein multiple wavelength ranges for individual pixels are separately detected, the synthetic image can be output as a hyperspectral image.

In yet other applications such as FLIM, a temporal behavior can be detected and analyzed by means of the SPSD, in particular a decay behavior of a fluorescent light source.

Another important application of the process is to implement a time-of-flight measurement using the SPSD. This can be achieved, for example, by known time-of-flight (ToF) methods wherein localized depth information is determined from an object area external to the image-recording device. In this case, a depth map of the object area can then be calculated from the depth information, which is of interest to certain applications. For this purpose, the image-recording device can also have a light signal source that emits the light pulses required for the ToF method.

The invention will now be described in more detail on the basis of exemplary embodiments, but is not limited to these exemplary embodiments. Further embodiments of the invention can be obtained from the following description of a preferred embodiment in connection with the general description, the claims, and the drawings.

In the following description of various preferred embodiments of the invention, elements with corresponding functions are given the same reference numbers, even if they have a different design or shape.

DRAWINGS

Figure 2:
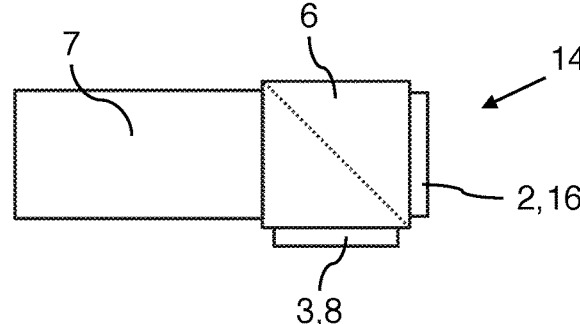
Figure 3:
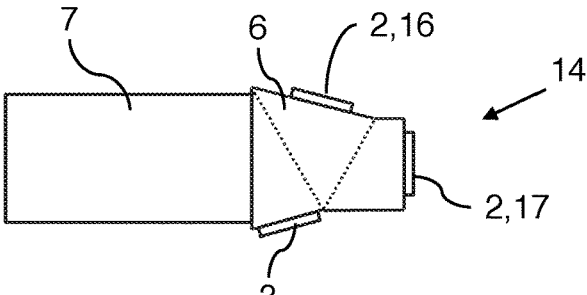
Figure 4:
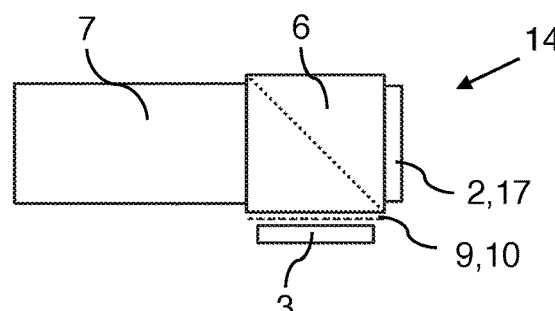
Figure 5:
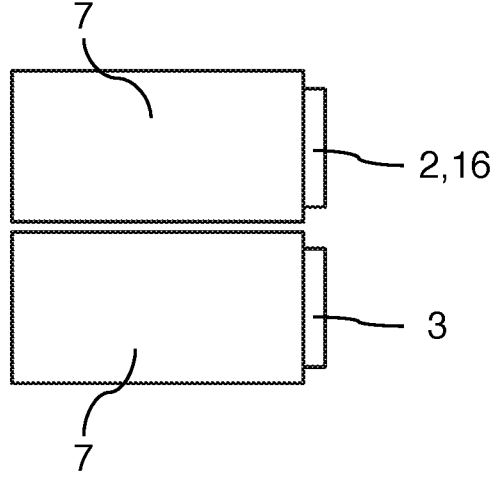
Figure 6:
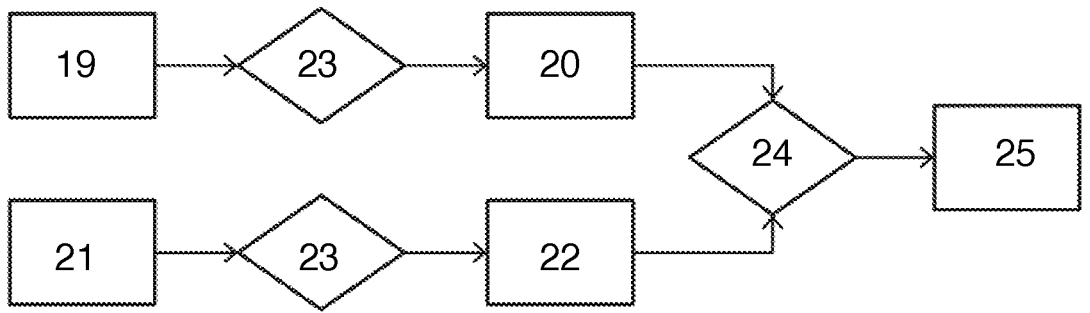
Figure 7:
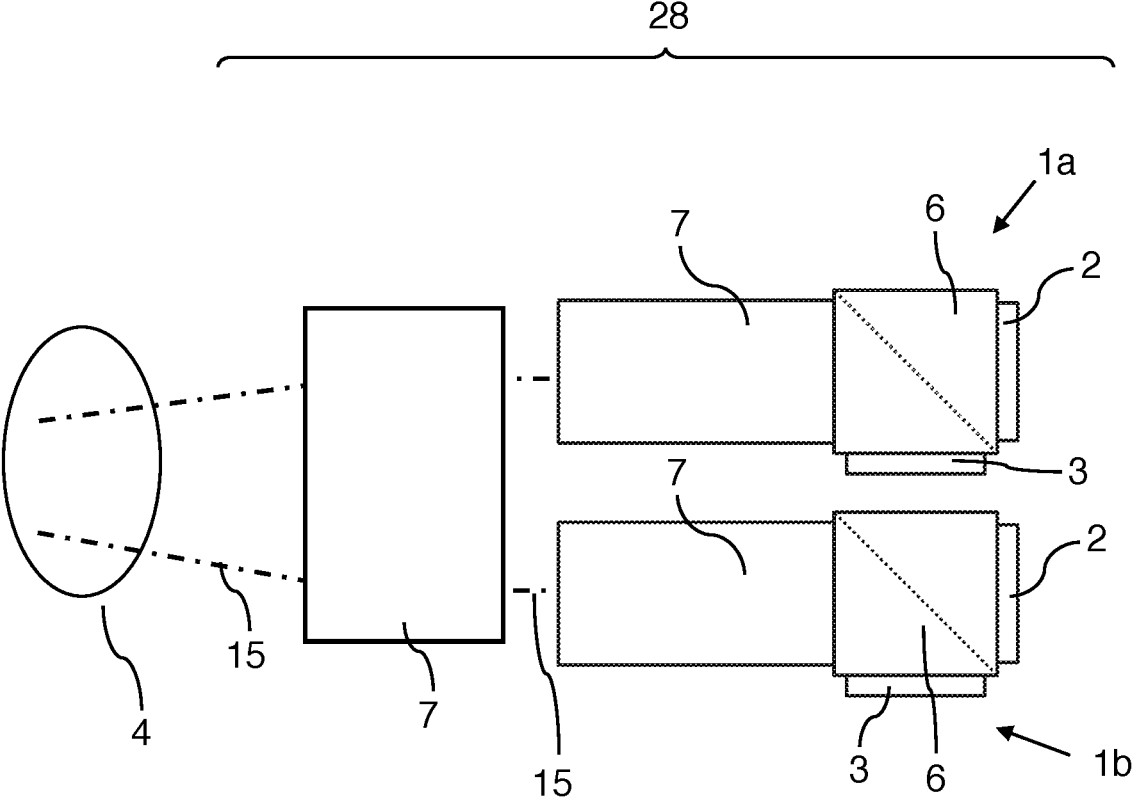

The present invention will be better understood from reading the following description of non-limiting embodiments, with reference to the attached drawings, wherein below:

FIG. 1 an endoscopic image-recording device according to an embodiment of the invention, FIGS. 2-4 respectively, different possible optical arrangements that can be used in an image-recording device according to the invention, FIG. 5 a further possible embodiment of an optical arrangement usable in an image-recording device according to the invention with two separate light guide channels, FIG. 6 a flow diagram illustrating an image-recording method according to the invention, and FIG. 7 a stereo image-recording device formed according to the invention.

DETAILED DESCRIPTION

FIG. 1 shows an image recording system 11 comprising an image-recording device 1 according to the invention, which is designed in the form of an endoscope 1, a camera control unit (CCU) 12, and a monitor 13 on which the images recorded with the endoscope 1 can be viewed. The camera control unit 12 in this case outputs the image data of the endoscope 1 to the monitor 13. The endoscope 1 has an optical arrangement 14 in its interior, which comprises an image sensor 2 as well as a single photon sensitive detector (SPS) 3, which can be formed as in the examples according to FIGS. 2-4 or as in FIG. 5.

In the example illustrated in FIG. 1, the optical arrangement 14 is arranged in a camera head 26 of the endoscope 1, i.e., straight on a proximal end of the endoscope 1. Accordingly, the endoscope 1 has an endoscope shaft 18 in which an optical imaging unit 7 is arranged. The optical imaging unit 7, can be used to transport image information from the object area 4 shown in FIG. 1 to the proximal end of the endoscope 1. The object area 4 can in this case be detected both with the image sensor 2 as well as with the SPSD 3.

Since the image sensor 2 is arranged at the proximal end, the endoscope shown in FIG. 1 is thus a chip-in-scope endoscope. However, an endoscope 1 according to the invention can also be formed as a chip-in-tip endoscope, wherein the optical arrangement 14 with the image sensor 2 and the SPSD 3 is then arranged in a distal end area 5 of the endoscope 1, i.e., for example at the end of the endoscope shaft 18.

As FIG. 1 shows, the light received from the common object area 4 is first transported through the (only schematically shown) optical imaging unit 7 to a beam splitter 6; this divides the image light into two separate beam paths, which lead once to image sensor 2 and once to SPSD 3. This ensures that there is a common object area 4 that lies outside of endoscope 1 and from which the light reaches to image sensor 2 and to the SPSD 3.

As shown in the example of FIG. 4, the optical arrangement 14 or the endoscope 1 can have an optical filter 9 so that the SPSD 3 can detect a spectral range that deviates from the one detected by the image sensor 2.

In the embodiment according to FIG. 4, the optical filter 9 is implemented on the beam splitter 6 as an optical thin film 10. Alternatively, such a filter 9 can also be formed in the working layer of the beam part 6 indicated by the dotted line, so that the beam splitter 6 is then dichroic.

If, on the other hand, the optical filter 9 is arranged, for example, at a distance from the beam splitter 6, it can in particular be formed to be actively tunable, so that—depending on the tuning of the optical filter 9—different wavelengths can be detected by the SPSD 3. Even in the optical path that leads to the optical image sensor 2, another optical filter 9 can be provided, for example to remove excitation light used to generate fluorescent light from the imaging.

The embodiments shown in FIGS. 2-4 but also in FIG. 5 each ensure that the image sensor 2 and the SPSD 3 are each arranged in a fixed spatial relationship to each other. In the embodiments according to FIG. 2 and FIG. 3, this is achieved in that the image sensor 2 and the SPSD 3 are each placed on outer surfaces of the beam splitter 6, corresponding to a common intermediate image plane, which is defined by the respective optical imaging unit 7. As a result, the beam splitter 6 forwards the light from the common object area 4 to the image sensor 2 as well as to the SPSD 3. Unlike in the example of FIG. 5, where two separate optical imaging units 7 are formed, the optical arrangements 14 according to FIGS. 2-4 thus only use a common light guide channel that conducts light from the common object area 4 to the beam splitter 6.

In the embodiment according to FIG. 3, the beam splitter 6 has a total of three exterior surfaces as well as two working layers (in each case illustrated by dotted lines) that split the incident light into three different beam paths. As can be seen, the optical arrangement 14 therefore also comprises a black-white image sensor 17 in addition to a color image sensor 16, with which additional image data can be recorded from the common object area 4.

When for example the black-white image sensor 17 is equipped with an additional filter 9 in FIG. 3, this image sensor 17 can detect a different spectral range than the color image sensor 16 (or also different than the SPSD 3).

FIG. 6 explains how the optical arrangements 14 of a respective endoscope 1 according to the invention, which are illustrated in FIGS. 2-5, can be used to implement an image-recording method according to the invention using the respective endoscope 1. In this case, a first image is first captured using one of the available image sensors 2. In more detail, raw data 19 of image sensor 2 is captured by means of an image computing unit 27 and processed into image data 20. For example, the image computation unit 27 can in this case be integrated in the image sensor 2 itself or can be located in a camera control unit (CCU) 12, and can thus also be located outside the image-recording device 1/the endoscope 1.

In parallel, raw data 21 that was recorded with the SPSD 3 is processed by the image computing unit 27 into additional image data 22. The image computing unit 27 then performs an image synthesis 24 in which the image data 20, 22 are computationally processed with each other, which can in particular take the form of an overlay, a false-color representation, or an image combination. The result of this calculation is a synthetic image 25, which can ultimately be viewed on the monitor 13.

One possible specific application, which can be implemented with the optical arrangement 14 according to FIG. 4, for example, is to collect 2D image data with the SPSD 3, and selectively, for example, in an NIR wavelength range that can pass through a filter 9 formed as a band-pass filter. At the same time, high-resolution image data 20 may be captured using the color image sensor 16. In this case, the color image sensor 16 can also have a cut-off filter, for example to filter out excitation light used for this fluorescent light imaging. By means of this approach, on the one hand, the fluorescent light can be detected selectively and with high light sensitivity using the SPSD 3 and can be used to enhance the 2D image data of the color image sensor 16 or to overlay additional image information with regard to the fluorescent light on the other hand. So that sensible 2D information can be obtained about the fluorescent light, the SPSD 3 is designed as a 2D single photon avalanche diode array (SPAD array). Here, the SPSD 3 is formed as a fully integrated electronic module/chip realized by means of silicon technology.

Due to the high light sensitivity of the SPSD 3, the endoscope 1 or the optical arrangement 14 can also be used to detect a decay of a fluorescent light source or to perform a time-of-flight (ToF) measurement, for example.

Lastly, FIG. 7 shows a stereo image-recording device 28, which has two image-recording devices 1a and 1b formed according to the invention, which are set up for stereoscopic vision/stereoscopic image capture using an additional optical imaging unit 7. This approach may be used to obtain 3D image data from the illustrated matching object region 4 observed by each of the two image-recording devices 1a and 1b.

In summary, in order to improve the imaging, in particular in the case of low light intensities, an image-recording device 1 is proposed, which is characterized in that the image-recording device 1 comprises a single photon sensitive detector (SPSD) 3 in addition to an image sensor 2, which uses photodiodes as light-sensitive cells, in order to capture light from a common object area 4. With the help of the SPSD 3, additional image information can be obtained from the object area 4, which can be used to enhance the image data recorded with the image sensor 2 or to enhance it with additional image information, in particular with regard to a further spectral range, which is captured with the SPSD 3.

What is claimed is:

1. An image recording device (1) arranged for medical imaging comprising:

at least one image sensor (2) whose pixels are based on photodiodes;

wherein the image recording device (1) has a single photon-sensitive detector (SPSD) (3) and the image sensor (2) and the SPSD (3) are arranged to detect light from a common object area (4);

wherein the image sensor (2) detects the light from the common object area (4) with the photodiodes;

wherein the SPSD (3) is a sensor device separate from the image sensor (2), the SPSD (3) is based on different individual detectors than the photodiodes of the image sensor (2), and the SPSD (3) offers higher sensitivity than the image sensor (2) for detecting the light from the common object area (4);

wherein the image recording device (1) has at least one optical filter (9) to keep undesired excitation light, used for fluorescence imaging and emanating from the object area (4), away from the SPSD (3).

2. The image recording device (1) according to claim 1, wherein the image sensor (2) and the SPSD (3) are arranged in a fixed spatial relationship to one another, with respect to a beam splitter (6); and wherein the beam splitter (6) passes light from the common object area (4) to the image sensor (2) and the SPSD (3), and wherein the image sensor (2) and the SPSD (3) are arranged on exterior surfaces of the beam splitter (6) and/or correspond to a common intermediate image plane of an optical imaging unit (7).

3. The image recording device (1) according to claim 1, wherein the image recording device (1) has a common optical imaging unit (7) arranged in a distal end area (5) of the image recording device (1), which conducts light from the common object area (4) to the image sensor (2) and to the SPSD (3).

4. The image recording device (1) according to claim 1, wherein the image recording device (1) forms two separate light guide channels, which each conduct light from the common object area (4) to the image sensor (2) or to the SPSD (3).

5. The image recording device (1) according to claim 1, wherein the image sensor (2) outputs a black and white image or a color image via a color filter array (CFA).

6. The image recording device (1) according to claim 1, wherein the image sensor (2) detects wavelengths in the visible range or alternatively wavelengths in adjacent wavelength ranges, in particular in the ultraviolet or infrared wavelength range.

7. The image recording device (1) according to claim 1, wherein the SPSD (3) is formed as a 2D arrangement of individual detectors that are fully-integrated and/or realized on the basis of semiconductor technology and can respectively detect individual photons so that the SPSD (3) provides 2D image data.

8. The image recording device (1) according to claim 1, wherein the SPSD (3) is implemented based on single photon avalanche diodes (SPADs) and/or silicon photomultipliers (SiPMs).

9. The image recording device (1) of claim 8 wherein the SPSD (3) is implemented as a 2D SPAD array or as a 2D SiPM array.

10. The image recording device (1) of claim 1, wherein the image sensor (2) and/or the SPSD (3) are implemented by means of CMOS technology as fully integrated electronic components, in particular with integrated signal processing electronics.

11. The image recording device of claim 1, wherein the at least one optical filter (9) keeps the undesired excitation light away from the image sensor (2).

12. The image recording device of claim 1, wherein the optical filter (9) selects a wavelength range captured by the SPSD (3) and/or the image sensor (2) and is implemented on the beam splitter (6) as an optical thin film (10).

13. The image recording device (1) according to claim 1, wherein the at least one optical filter (9) is actively tunable such that different wavelengths can be detected by the SPSD (3) depending on the tuning of the optical filter (9).

14. The image recording device (1) according to claim 1, wherein the image recording device (1) has at least two separately arranged SPSDs (3) that detect different wavelength ranges via two different optical filters (9).

15. The image recording device (1) according claim 1, wherein the image recording device (1) has at least two image sensors (2) arranged separately from each other that detect different wavelength ranges via different color filters at the pixel level.

16. The image recording device (1) according to claim 1, wherein the image recording device (1) has an image computing unit (27) that is designed to calculate and output a synthetic image from signals of the image sensor (2) and from signals of the SPSD (3).

17. A stereo image recording device (28) for generating 3D image data that includes a a stereo image recording device (1) having two image recording devices (1) according to claim 1; and wherein the two image recording devices (1) are arranged for stereoscopic imaging, such that 3D image data can be obtained from a matching object area.

18. An image recording method using an image recording device (1) of claim 1, wherein recording a first image, preferably a color image, by means of an image sensor (2) of the image recording device (1), whose pixels are based on photodiodes;

recording a second image using a single photon sensitive detector (SPSD) of the image recording device (1); and calculating and outputting a synthetic image from the first image and the second image, wherein autofluorescent light is detected with the SPSD (3) and wherein excitation light used for fluorescence imaging is separated and filtered from the fluorescent light by an optical filter (9) before the fluorescent light reaches the SPSD (3).

19. The image recording method according to claim 18, wherein the second image is scaled to an image resolution of the first image prior to synthesis.

20. The image recording method according to claim 18, wherein the synthetic image is obtained by uniting the first image with the second image by means of an alpha-blending method, wherein alpha values are taken into account in addition to color information as a metric for the transparency or opacity of respective pixels.

21. The image-recording method according to claim 18, wherein at least a third image in an additional wavelength range, captured via an additional image sensor (2) or an additional SPSD (3) of the image recording device (1), is taken into account during the synthesis of the synthetic image, and the synthetic image is output as a hyperspectral image.

22. The image-recording method according to claim 18, wherein a decay behavior of a fluorescent light source, is detected and evaluated by means of the SPSD (3).

23. The image-recording method according to claim 18 wherein a time of flight measurement is implemented using the SPSD (3) by means of a time-of-flight (ToF) method by which location-resolved depth information is determined from an object area (4) outside of the image recording device (1).

24. An image recording method using an image recording device (1) of claim 1, comprising:

the image sensor (2) whose pixels are based on photodiodes;

the SPSD (3) offering higher sensitivity than the image sensor (2);

wherein in a first step:

a first fluorescence image is captured with the SPSD (3) and superimposed on a white light image recorded with the image sensor (2) to enable the detection of weak fluorescent light sources in deeper tissue layers, and the first fluorescence image, due to its low signal intensity, is not visible in the white light image recorded with the second image; and subsequently in a second step:

a spatially high-resolution second fluorescence image is captured with the image sensor (2) to enable examination of a fluorescent tissue, which has been detected in the first step, in higher spatial resolution using the image sensor (2).

* * * * *